United States Patent [19]
Sauer et al.

[11] Patent Number: 6,139,319
[45] Date of Patent: *Oct. 31, 2000

[54] METHOD AND DEVICE FOR THE CLEANSING AND CARE OF THE TEETH AND GUMS

[75] Inventors: Michael Sauer, Bad Camberg; Norbert Schaefer, Frankfurt; Michael Stolper, Eschborn, all of Germany

[73] Assignee: Braun GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/986,232

[22] Filed: Dec. 5, 1997

[30] Foreign Application Priority Data

Dec. 23, 1996 [DE] Germany .............................. 196 54 099

[51] Int. Cl.⁷ .............................. A61G 17/02; A61C 15/00
[52] U.S. Cl. .............................. 433/80; 433/216; 601/162; 601/163; 601/165
[58] Field of Search .............................. 433/80, 88, 216, 433/215; 601/162, 163, 165

[56] References Cited

U.S. PATENT DOCUMENTS

| | | |
|---|---|---|
| 3,739,983 | 6/1973 | Jousson . |
| 3,828,771 | 8/1974 | Gartner .................................. 601/165 |
| 4,159,715 | 7/1979 | Woog et al. ............................ 601/162 |
| 4,941,459 | 7/1990 | Mathur .................................... 601/165 |
| 5,511,693 | 4/1996 | Weissman et al. ......................... 222/1 |

FOREIGN PATENT DOCUMENTS 35 45 868 A1  6/1987  Germany .

*Primary Examiner*—Nicholas D. Lucchesi
*Attorney, Agent, or Firm*—Fish & Richardson P.C.

[57] ABSTRACT

The invention is directed to a jet nozzle (1) for a handpiece of an oral irrigator, which has a nozzle head (2) in which a feed line (4) runs. The feed line (4) opens into an outlet orifice (5) from which a liquid can emerge in the form of a single jet. A constriction (6) is provided in the feed line (4). The constriction (6) acts to produce a large number of microfine gas bubbles. The microfine gas bubbles are better suited to penetrate deep into subcrestal pockets in order to kill anaerobic bacteria which have settled there by the supply of oxygen, hence treating and curing inflammations of the gums.

33 Claims, 2 Drawing Sheets

METHOD AND DEVICE FOR THE CLEANSING AND CARE OF THE TEETH AND GUMS

BACKGROUND OF THE INVENTION

This invention relates to a method for the cleansing and care of the teeth and gums, comprising the step of conveying a liquid to and discharging it from an outlet orifice, and to a jet nozzle for a device for the cleansing and care of the teeth and gums, particularly for a handpiece of an oral irrigator, with a nozzle head in which a feed line runs which opens into an outlet orifice from which a liquid can emerge.

A method of this type and a jet nozzle of this type are known from European Patent No. EP 0 175 881 B2. This patent contains a description of an electrically powered oral irrigator for oral and dental hygiene, which includes a handpiece to which a jet nozzle is attachable. The jet nozzle is equipped with a nozzle head in which a feed line runs from an inlet, which is connected to the handpiece, to an outlet. When the oral irrigator is switched on, water is pumped via the handpiece to the jet nozzle and hence to the nozzle head. Here the water emerges in the form of a single jet from the outlet. This single jet can be employed by the user to care for and cleanse his teeth and gums. The single jet is suitable in particular for clearing food particles or the like from the subcrestal pockets between the teeth and the gums.

It is known furthermore that inflammations of the gums such as gingivitis or periodontitis are caused by bacteria. The bacteria involved are mainly anaerobic bacteria which settle in the subcrestal pockets in particular. A distinction is made between facultative anaerobic bacteria such as actinobacillus actinomycetemcomitans, which can live in an atmosphere of air, and strict anaerobic bacteria such as porphyromonas gingivalis, which can survive only in the absence of oxygen.

Experience has shown that in both cases a supply of oxygen can permanently disturb or even end particularly the growth of the bacteria. This can result ultimately in the death of the bacteria and hence in the treatment and cure of inflamed gums.

For this to happen it is necessary to confront the bacteria with as much oxygen as possible. This means that as much oxygen as possible has to be conveyed as deeply as possible into the subcrestal pockets in order to be able to disturb the bacteria there in their growth.

Ordinary tap water has an oxygen content of about 40% up to about 80% saturation, corresponding to about 3–8 mg/l oxygen in the temperature range from 20° C. to 40° C. This has been discovered to be too little oxygen for the successful treatment and cure of inflamed gums.

It is also possible to add air to the water by having the pump draw in not only the liquid but also air, for example, and conveying it to the outlet. In this case, however, it has been discovered that because of the great difference in the density of water and air the two substances separate again very quickly so that the air escapes again. The air and hence the oxygen thus fails to get into the subcrestal pockets and is unable therefore to contribute to the treatment or cure of inflamed gums.

A further possibility is to blow gaseous oxygen directly into the subcrestal pockets. However, this involves the risk of embolism for the user, meaning that the pressure permitted is so very low as to be incapable of clearing food particles and the like from the subcrestal pockets.

With all the options described above it has been impossible so far to successfully combine the cleansing and flushing effect of water with the curative effect of oxygen.

SUMMARY OF THE INVENTION

It is an object of the present invention to provide a method and a jet nozzle of the type initially referred to, with which it is possible to cleanse and care for the teeth and gums and also to treat and cure inflammations situated deep in the subcrestal pockets.

This object is accomplished by the present invention in that in a method of the type initially referred to microfine gas bubbles are produced in the liquid.

The microfine gas bubbles have very small dimensions, in particular in the range of a few micrometers. Consequently, the buoyancy of the microfine gas bubbles in the liquid is very low. Essentially, therefore, there is no separation of the microfine gas bubbles from the liquid. Hence the microfine gas bubbles are maintained in the liquid and do not escape.

In a device for the cleansing and care of the gums and teeth it is possible by this means to introduce microfine gas bubbles containing oxygen in the water. As explained, this oxygen remains in the water and is thus able, together with the water, to penetrate deep into the subcrestal pockets. Here the water exerts its known cleansing effect, removing food residues and the like. The oxygen, which is conveyed simultaneously into the subcrestal pockets by means of the microfine gas bubbles, can exert a curative effect on any inflammations of the gums that may be present by disturbing or even ending the growth of the bacteria causing the inflammation.

It has been found that the amount of oxygen confronting the bacteria on account of the microfine gas bubbles is so high as to actually achieve a successful treatment and cure of any inflammations of the gums.

As a result of the present invention, the cleansing and flushing effect of water is thus combined with the curative effect of oxygen. An oral irrigator is made available that not only enables the teeth and the gums to be cleansed and cared for but also enables a curative effect to be exerted on any inflammations of the gums as the result of the microfine gas bubbles.

In a particularly advantageous embodiment of the present invention, the microfine gas bubbles are produced in such a way that they remain in the liquid as long as possible after emerging from the outlet orifice. Particularly suitably, the microfine gas bubbles are produced in such a way that they remain in the liquid after emerging from the outlet orifice until they reach the subcrestal pockets between the teeth and the gums. This has the advantage of the microfine gas bubbles with the oxygen actually remaining in the liquid until they reach those local points in the subcrestal pockets where the inflammation-inducing bacteria have settled. This ensures that the curative effect of the oxygen is able to work with full impact.

In a further particularly advantageous embodiment of the present invention, the microfine gas bubbles are produced with a diameter of up to about 200 $\mu$m, particularly with a diameter in the range from about 1 $\mu$m to about 50 $\mu$m.

Tests have revealed that separation of the oxygen from the liquid takes place slowly again with microfine gas bubbles having a diameter larger than about 200 $\mu$m. Hence the use of microfine gas bubbles with a diameter of up to about 200 $\mu$m guarantees that the oxygen remains in the liquid and is thus able to penetrate deep into the subcrestal pockets together with the liquid.

With a diameter smaller than about 50 $\mu$m it was possible in the tests to obtain a particularly large number of microfine gas bubbles. This is particularly advantageous because with a large number of microfine gas bubbles it is possible to convey a large volume of oxygen into the subcrestal pockets.

In a particularly advantageous further feature of the present invention, approximately the middle 80% of the microfine gas bubbles are produced with a diameter in the range from about 4 µm to about 22 µm. The latter value may lie in a range from about 20 µm to about 25 µm. Hence the majority of the microfine gas bubbles has a diameter of between about 4 µm and about 22 µm. In the tests it was discovered that with the help of this approximately 80% share of the microfine gas bubbles a sufficient volume of oxygen gets into the subcrestal pockets in order to successfully treat any inflammations of the gums to be found there.

In another particularly advantageous further feature of the present invention, about 50% of the microfine gas bubbles are produced with a diameter of less than about 11 µm. This value, which if necessary may also lie in a range from about 10 µm to about 12 µm, was found in the tests to be a particularly advantageous diameter for the microfine gas bubbles. In particular it was found that the number of microfine gas bubbles reaches a maximum at this diameter value. The number of microfine gas bubbles with a diameter of about 11 µm is therefore greater than the number with a larger or smaller diameter.

In a particularly advantageous embodiment of the present invention, the microfine gas bubbles are produced by means of a pressure exerted on the liquid. This utilizes the fact that the more oxygen can be dissolved in water, for example, the more pressure is exerted on the water. Hence with the help of pressure, the oxygen content in the water is increased by particularly simple means.

In a particularly advantageous further feature of the present invention, the microfine gas bubbles are produced by means of a constriction arranged upstream of the outlet orifice. The constriction causes the conveyed liquid, which is flowing to the outlet, to be banked up. At the same time this means that the pressure acting on the liquid upstream of the constriction is increased. This pressure increase has the above described effect of enabling more oxygen to be dissolved in the liquid. On the whole, therefore, the oxygen content in the liquid is increased in particularly simple manner by means of the constriction.

When the liquid carrying the oxygen reaches the constriction, the liquid is suddenly relieved as it passes through the constriction. Consequently the oxygen is degassed from the liquid in the form of microfine gas bubbles. The microfine gas bubbles then contained in the liquid downstream of the constriction are conveyed with the liquid into the subcrestal pockets.

Particularly suitably, a pressure in a range from about 2 bar to about 20 bar is generated, in particular a pressure in a range from about 5 bar to about 8 bar. The higher the pressure acting on the liquid, the better the microfine gas bubbles can be produced. On the other hand, the pressure should not be too high or injuries to the gums may be caused by the impinging liquid jet. Pressure in a range from about 5 bar to about 8 bar has proven to be particularly advantageous in the tests.

In another particularly advantageous embodiment of the present invention, the microfine gas bubbles are produced by stirring of the liquid in a whirl-type action. In this embodiment it is particularly suitable if the liquid is subsequently compressed.

In another particularly advantageous embodiment of the present invention, the microfine gas bubbles are produced by chopping the liquid. This can be accomplished in particular by directing the liquid through an aperture which is opened and closed in cycles.

The above mentioned possibilities of producing microfine gas bubbles may be used singly or in combination. It is also possible to produce such gas bubbles by means of the "bubble-through" principle, which finds application on water faucets. The special bubble-through construction may have to be appropriately modified, however, to produce the microfine gas bubbles.

With all these possibilities it is particularly suitable to convey the liquid in a continuous or quasi-continuous stream to the outlet orifice. In the tests performed this has proven to be particularly advantageous with regard to the formation of microfine gas bubbles.

The object initially identified is also accomplished by the present invention in that in a jet nozzle of the type initially referred to a constriction is provided in the feed line. As already explained, the liquid is banked up in the feed line upstream of the constriction, causing the pressure on the liquid to be increased. This has the effect of enabling more oxygen to be dissolved in the liquid. Upon passing through the constriction the oxygen is degassed from the liquid and the microfine gas bubbles are formed. These microfine gas bubbles are then able to penetrate together with the cleansing liquid deep into the subcrestal pockets in order to exert their curative effect there.

Furthermore, the constriction in the feed line causes the speed of the liquid flowing through the feed line to be increased. In this sense the constriction acts like a venturi nozzle. The increased flow rate of the liquid downstream of the constriction and particularly the attendant pressure drop occurring immediately downstream of the constriction results in gas cavitation in the liquid. Consequently, any large gas bubbles contained in the liquid are atomized into numerous parts, thus increasing the number of gas bubbles and reducing the volume of the individual gas bubbles.

If air is added to the liquid upstream of the constriction by some means or other, for example by having not only water but also air drawn in and conveyed toward the constriction by the pump, the water will contain this air in the form of large gas bubbles. As previously described, these large gas bubbles are atomized into numerous parts by the constriction so that ultimately microfine gas bubbles are formed from these large gas bubbles as well.

On the whole this results in a very uniform distribution of microfine gas bubbles in the liquid. Consequently the liquid emerging from the jet nozzle is equally uniformly mixed with microfine gas bubbles.

As explained in the foregoing, microfine gas bubbles of this type have been found to 'live' far longer than large gas bubbles. This means that microfine gas bubbles remain tied up in the liquid far longer than large gas bubbles, accordingly leaving the liquid far later.

If, in the case of an oral irrigator, a jet of water carrying the microfine gas bubbles is now directed at the subcrestal pockets in particular, the microfine gas bubbles penetrate deeper into the subcrestal pockets than large gas bubbles. Hence it is possible for any anaerobic bacteria that have settled deep in the subcrestal pockets to be struck by the microfine gas bubbles. As a result of the present invention, therefore, the oxygen contained in the gas bubbles is also able to reach any inflammations existing deep in the subcrestal pockets. With the aid of the oral irrigator of the present invention it is also possible, therefore, to attack any bacteria that have settled deep in the subcrestal pockets and hence to treat and cure inflammations of the gums.

In an advantageous embodiment of the present invention, the feed line has an approximately circular cross section, and the constriction is formed as an inwardly protruding annular projection. This represents a very simple and, with regard to the jet nozzle's manufacture, expedient configuration of the constriction.

In a further advantageous embodiment of the present invention, the constriction has the smallest possible extension in the direction of movement of the liquid. In this manner, the formation of the microfine gas bubbles is significantly improved, particularly with regard to their size and number.

In an advantageous further feature of the present invention, the feed line has an inner diameter in a range from about 0.5 mm to about 0.9 mm, preferably about 0.7 mm, and the constriction has an inner diameter in a range from about 0.2 mm to about 0.5 mm, preferably about 0.4 mm. These values for the constriction's dimensions have proven to be particularly advantageous with a view to forming the microfine gas bubbles.

In a further advantageous feature of the present invention, the relative distance of the constriction to the outlet orifice is in a range from about 2 mm to about 80 mm, preferably in a range from about 4 mm to about 10 mm. Hence the constriction is not necessarily positioned directly at the outlet of the jet nozzle but is set a distance away from the outlet. This has also proven advantageous with a view to forming the microfine gas bubbles.

In an advantageous embodiment of the present invention, the feed line is made of plastic and the constriction is obtained by means of a forming operation, in particular a hot forming operation. This represents a particularly simple and economical way to manufacture the jet nozzle.

BRIEF DESCRIPTION OF THE DRAWINGS

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference. In the drawings.

DESCRIPTION OF THE PREFERRED EMBODIMENTS

Figure 1:
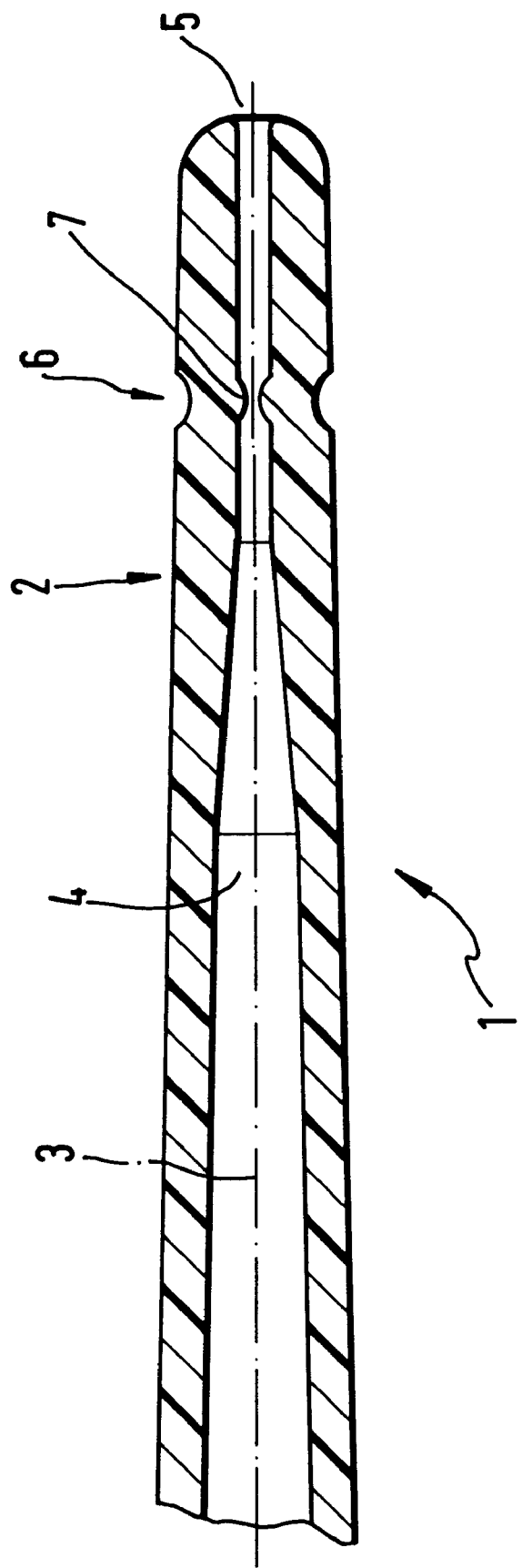
FIG. 1 is a schematic longitudinal sectional view of an embodiment of a jet nozzle constructed in accordance with the present invention.

FIG. 1 shows a jet nozzle 1 for an oral irrigator. The jet nozzle 1 is releasably attachable to a handpiece which is connected by a hose to the oral irrigator. The oral irrigator has a liquid reservoir which can be filled with water by the user. A pump driven by an electric motor is accommodated in the housing of the oral irrigator and can be used for pumping the water from the liquid reservoir through the hose to the handpiece and hence to the jet nozzle 1.

When the oral irrigator is switched on, the water jet produced by the jet nozzle can be used by the user to care for and clean his teeth and gums. The water jet can be pulsating or rotating or preferably continuous or quasi-continuous.

The jet nozzle 1 has a nozzle head 2 of an approximately tubular configuration extending in the direction of a longitudinal axis 3. A feed line 4 runs in the direction of the longitudinal axis 3 inside the nozzle head 2. The feed line 4 opens into an outlet orifice 5 at the free end of the nozzle head 2. When the oral irrigator is switched on, a single water jet emerges from the outlet orifice 5.

The feed line 4 has an approximately circular cross section diminishing along the longitudinal axis 3 in the direction of the outlet orifice 5. The inner diameter of the feed line 4 is approximately constant in the area upstream of the outlet orifice 5. In this area the feed line 4 has a constriction 6.

In the area of the constriction 6 the feed line 4 has an inner diameter of about 0.7 mm. The constriction 6 is configured as an inwardly protruding annular projection 7 having an inner diameter of about 0.4 mm. The relative distance of the constriction 6 to the outlet orifice 5 is about 6 mm. The amount of extension of the projection 7 and hence the extension of the constriction 6 in the direction of the longitudinal axis 3, that is, in the direction of movement of the water, is as small as possible.

The jet nozzle 1 is made of plastic, the constriction 6 being obtained by hot forming of the plastic. Alternatively, the constriction 6 can be fitted in the nozzle head 2 as a separate component made of metal or plastic.

When the oral irrigator is switched on the water is pumped from the liquid reservoir to the jet nozzle 1. The water thus flows through the feed line 4 toward the constriction 6. On account of the constriction 6 the water is banked up in the feed line 4 upstream of the constriction 6. This causes an increase in the pressure acting on the water and hence an increase in the oxygen dissolved in the water.

On passing through the constriction 6 the water is suddenly relieved. This causes the oxygen dissolved in the water to be degassed from the water, forming microfine gas bubbles in the water.

Further, any large gas bubbles that were already introduced in the water upstream of the constriction as by the admixture of air and which are therefore to be found in the water, are atomized into numerous parts by the constriction 6. This results in the formation of a large number of additional microfine gas bubbles.

The microfine gas bubbles produced from the dissolved oxygen and the microfine gas bubbles formed by dividing any large bubbles are then uniformly contained in the water downstream of the constriction 6.

When the oral irrigator is used by a user for cleansing his subcrestal pockets in particular, the microfine gas bubbles remain in the water until deep in the subcrestal pockets. Hence the oxygen contained in the microfine gas bubbles also reaches the anaerobic bacteria which have settled deep in the subcrestal pockets. The inflammations of the gums caused by such bacteria can be treated and cured by transporting the oxygen to the anaerobic bacteria.

Instead of the constriction 6 for producing the microfine gas bubbles it is also possible to provide a whirl-type device stirring or beating the water in order to introduce air or oxygen in the water. Subsequently, the water can be compressed and nebulized or atomized. A further possibility of producing the microfine gas bubbles is to chop the water. This can be accomplished, for example, by directing the water already containing air bubbles or oxygen through an aperture which is opened and closed in cycles. The aperture can be fitted with a circumferential diaphragm or the like for this purpose.

Figure 2:
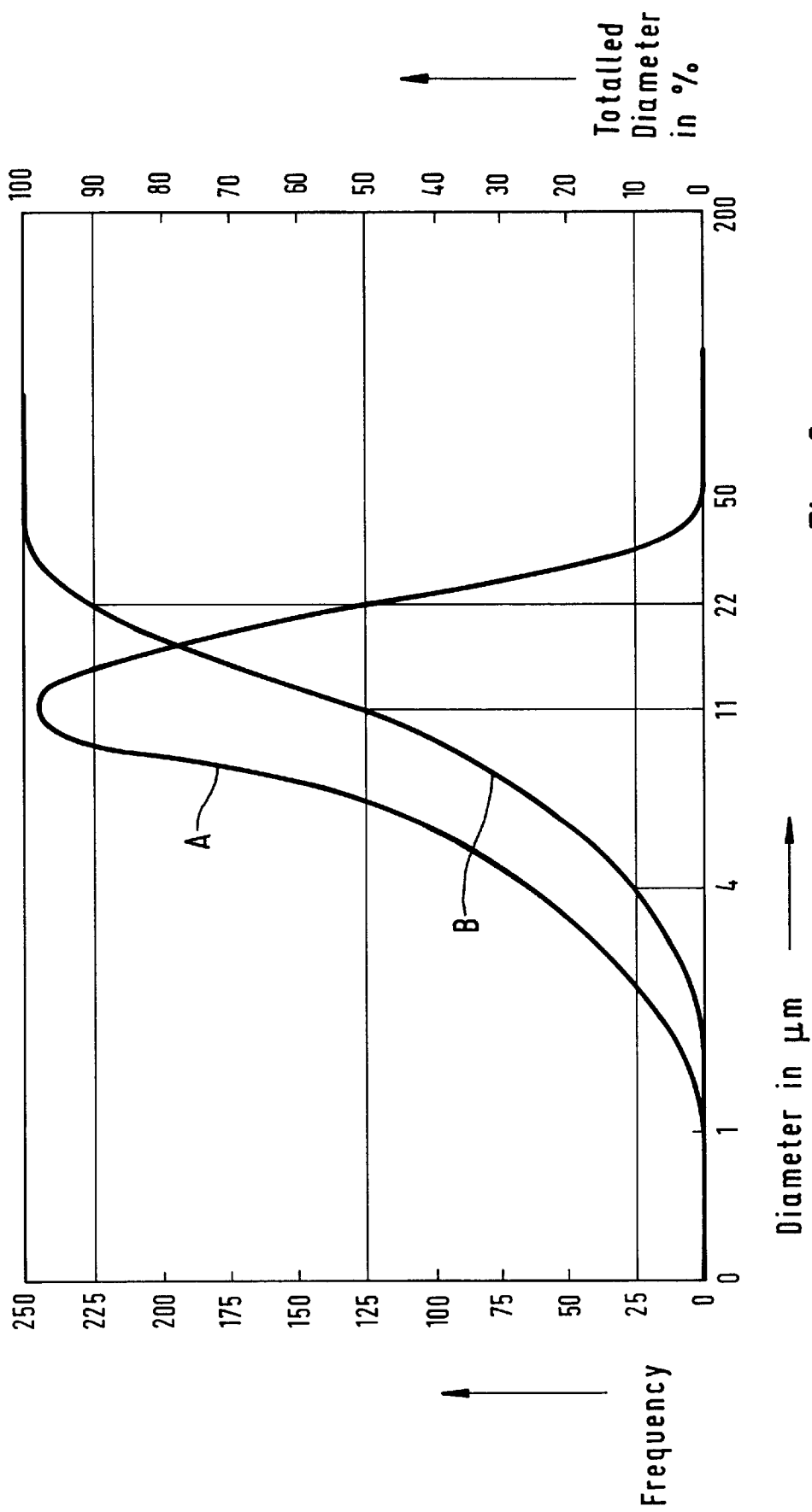
FIG. 2 is a schematic diagram showing two curves relating to the formation of microfine gas bubbles.

FIG. 2 shows a diagram with two curves A and B, which were determined by means of tests. In the tests the formation of microfine gas bubbles was influenced, for example, by varying the constriction 6, particularly by varying the diameter of the constriction 6. The number and the diameters of the formed microfine gas bubbles were then measured for a predetermined period of time and processed to form the curves A and B.

The diameter of the microfine gas bubbles in μm is plotted on the abscissa of the diagram for both curves A and B. For curve A the frequency of the microfine gas bubbles in absolute numbers is plotted on the ordinate, and for curve B the aggregate diameter in % is plotted on the ordinate.

Curve A thus shows how many microfine gas bubbles with a certain diameter are present, and curve B shows essentially the integral over curve A and hence a measure of the volume transported by the microfine gas bubbles.

As becomes apparent from curve A, the microfine gas bubbles have a diameter of between about 1 μm and about 50 μm. The greatest frequency of microfine gas bubbles occurs at a diameter of between about 10 μm and about 12 μm, particularly at a diameter of about 11 μm.

In the tests it was also found that microfine gas bubbles with a diameter from about 200 μm and bigger are not held in the water but separate again very quickly, escaping from the water.

In curve B the diameters of the microfine gas bubbles are totaled according to their respective frequency and then plotted as a percentage. Hence curve B ascends continuously from 0. Curve B shows the value 100% when all the microfine gas bubbles are totaled. This is the case at a microfine gas bubble diameter of about 50 μm.

From curve B it appears that the microfine gas bubbles with a diameter smaller than about 11 μm transport about 50% of the maximum possible volume. The other half of the volume is accounted for by the microfine gas bubbles with a larger diameter.

As becomes further apparent from curve B, about 80% of the maximum possible volume is transported by microfine gas bubbles with a diameter of between about 4 μm and about 22 μm. The latter value may also vary between about 20 μm and about 25 μm. This represents the middle 80% of the maximum volume that can be transported by the microfine gas bubbles, supplemented by a 10% volume contribution from the microfine gas bubbles with a diameter smaller than 4 μm and a 10% volume contribution from the microfine gas bubbles with a diameter larger than 22 μm.

From the synopsis of curves A and B it becomes apparent, on the one hand, that the microfine gas bubbles with a larger diameter make a bigger contribution to the volume but, on the other hand, that the frequency of these large microfine gas bubbles decreases as the diameter increases. Moreover, it appears from curves A and B that as the diameter of the microfine gas bubbles decreases, so the frequency and the transported volume also decrease.

This results in a preferred range for the diameter of the microfine gas bubbles which lies roughly between 4 μm and about 22 μm or about 30 μm. A particularly advantageous diameter for the microfine gas bubbles lies at about 11 μm.

What is claimed is:

1. A method for the cleansing and care of the teeth and gums comprising:
    supplying a liquid;
    introducing air into the liquid;
    after introducing air into the liquid, conveying the liquid to and discharging it from an outlet orifice;
    downstream from where the air is introduced into the liquid, causing the air within the liquid to produce microfine gas bubbles in the liquid that discharges from the outlet orifice.

2. The method according to claim 1, wherein the microfine gas bubbles are produced in such a way that during use for cleansing teeth they remain in the liquid after emerging from the outlet orifice until they reach the subcrestal pockets between the teeth and the gums.

3. The method according to claim 1, wherein a majority of the microfine gas bubbles that are produced have a diameter in the range from about 1 μm to about 50 μm.

4. The method according to claim 1, wherein approximately the middle 80% of the microfine gas bubbles that are produced have a diameter in the range from about 4 μm to about 30 μm.

5. The method according to claim 1, wherein about 50% of the microfine gas bubbles that are produced have a diameter of less than about 11 μm.

6. The method according to claim 1, wherein the producing step comprises exerting a pressure on the liquid to produce the microfine gas bubbles.

7. The method according to 6, wherein the producing step further comprises passing the pressurized liquid through a constriction arranged upstream of the outlet orifice to produce the microfine bubbles.

8. The method according to claim 7, wherein the pressure is in a range from about 2 bar to about 20 bar.

9. The method according to claim 7, wherein the pressure is in a range from about 5 bar to about 8 bar.

10. The method according to claim 1, wherein the air introducing step comprises stirring the liquid in a whirl-type action to add the air to the liquid.

11. The method according to claim 10, wherein the producing step comprises compressing the liquid containing the air.

12. The method according to claim 11, wherein the producing step further comprises directing the liquid through an aperture which is opened and closed in cycles.

13. The method according to claim 1, wherein the producing step comprises chopping the liquid to produce the microfine gas bubbles.

14. The method according to claim 1, wherein the conveying step comprises conveying the liquid to the outlet orifice in a continuous or quasicontinuous stream.

15. A jet nozzle for an oral irrigator, said nozzle comprising:
    a nozzle head having a feed line which opens into an outlet orifice from which a liquid emerges during use, wherein said feed line contains a constriction which during use acts on the liquid passing through the constriction to produce microfine gas bubbles in the liquid; and
    an air-introducing means for introducing air into the liquid before the liquid reaches the constriction.

16. The jet nozzle according to claim 15, wherein the feed line has an approximately circular cross section, and the constriction is formed as an inwardly protruding annular projection.

17. The jet nozzle according to claim 16, wherein the feed line has an inner diameter in a range from about 0.5 mm to about 0.9 mm and the constriction has an inner diameter in a range from about 0.2 mm to about 0.5 mm.

18. The jet nozzle according to claim 16, wherein the feed line has an inner diameter in a range from about 0.5 mm to about 0.7 mm.

19. The jet nozzle according to claim 16, wherein the constriction has an inner diameter in a range from about 0.2 mm to about 0.4 mm.

20. The jet nozzle according to claim 15, wherein the constriction has the smallest possible extension in the direction of movement of the liquid.

21. The jet nozzle according to claim 15, wherein the distance from the constriction to the outlet orifice is in a range from about 2 mm to about 80 mm.

22. The jet nozzle according to claim 15, wherein the feed line is made of plastic and the constriction is produced by a forming operation.

23. A device for the cleansing and care of the teeth and gums, with a jet nozzle according to claim 15.

24. The jet nozzle according to claim 15, wherein the distance from the constriction to the outlet orifice is in a range from about 4 mm to about 10 mm.

25. The jet nozzle according to claim 15, wherein the feed line is produced by a hot forming operation.

26. A method for the cleansing and care of the teeth and gums comprising:

conveying a liquid to and discharging it from an outlet orifice;

introducing air into the liquid before it is discharged from the orifice;

after introducing air into the liquid, producing microfine gas bubbles in the liquid; and discharging the liquid with the microfine gas bubbles from the outlet orifice, wherein a majority of the microfine bubbles produced have a diameter less than about 50 μm.

27. A method for the cleansing and care of the teeth and gums comprising:

conveying a liquid to and discharging it from an outlet orifice;

introducing air into the liquid before it is discharged from the orifice;

after introducing air into the liquid, producing microfine gas bubbles in the liquid; and discharging the liquid with the microfine gas bubbles from the outlet orifice, wherein about 80% of the microfine bubbles that are produced have a diameter in the range of about 4 μm to about 30 μm.

28. A method for the cleansing and care of the teeth and gums comprising:

conveying a liquid to and discharging it from an outlet orifice;

introducing air into the liquid before it is discharged from the orifice;

after introducing air into the liquid, producing microfine gas bubbles in the liquid; and discharging the liquid with the microfine gas bubbles from the outlet orifice, wherein about 50% of the microfine bubbles produced have a diameter less than about 11 μm.

29. A method for the cleansing and care of the teeth and gums comprising:

conveying a liquid to an outlet orifice;

introducing air into the liquid being conveyed to the outlet orifice;

after introducing air into the liquid producing microfine gas bubbles from the air that was introduced into the liquid; and discharging the liquid and the microfine bubbles produced therein from the outlet orifice.

30. The method of claim 29 wherein the step of introducing air comprises dissolving air in the liquid and wherein the step of producing microfine bubbles comprises causing the dissolved air to degas from the liquid.

31. The method of claim 30 wherein the causing dissolved air to degas from the liquid comprises passing the liquid with the dissolved air through a constriction.

32. The method of claim 24 wherein the step of producing microfine bubbles is accomplished by gas cavitation.

33. The method of claim 29 wherein the step of introducing air into the liquid comprises forming macro gas bubbles and wherein the step of producing microfine gas bubbles comprises atomizing the macro gas bubbles to form the microfine gas bubbles, wherein the macro gas bubbles are larger than the micro gas bubbles.

* * * * *